United States Patent [19]

Bodor

[11] 4,021,546
[45] May 3, 1977

[54] PRO-DRUG FORMS OF DIGOXIN AND METHOD OF PREPARING AND USING SAME

[75] Inventor: Nicolae S. Bodor, Lawrence, Kans.

[73] Assignee: Interx Research Corporation, Lawrence, Kans.

[22] Filed: Mar. 8, 1976

[21] Appl. No.: 664,687

[52] U.S. Cl. .................................. 424/182; 536/7
[51] Int. Cl.² .................................. A61K 31/705
[58] Field of Search .............. 260/210.5; 424/182; 536/7

[56] References Cited
UNITED STATES PATENTS 3,884,905  5/1975  Bodor .......................... 260/210.5

Primary Examiner—Lewis Gotts
Assistant Examiner—Cary Owens
Attorney, Agent, or Firm—Charles N. Blitzer

[57] ABSTRACT

There is provided, a novel pro-drug form of digoxin having the following formula:

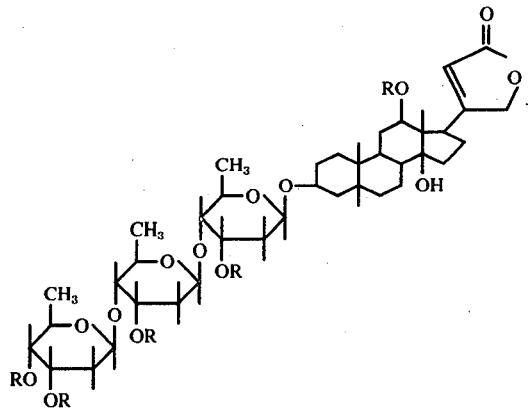

wherein R represents a member selected from the group consisting of a hydrogen atom, a residue of any naturally occurring amino acid, and a

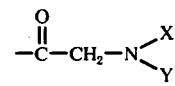

group, wherein X and Y, which may be the same or different, each represent a member selected from the group consisting of a methyl group and an ethyl group, or wherein X and Y may form a $(CH_2)_4$ or $(CH_2)_5$ heterocyclic ring with the N atom to which each of X and Y are attached, and a non-toxic inorganic or organic pharmaceutically acceptable acid addition salt thereof, with the proviso that:

when R is a member other than a hydrogen atom, all of said R's must be the same member.

These novel compounds will be cleaved in the bloodstream of a warm-blooded animal, thus delivering digoxin in a cardiotonic effective amount. Due to their higher solubility and superior absorption characteristics, the compounds of the instant invention permit a higher and more reproducible level of digoxin bioavailability to be attained in comparison with that which could be attained if digoxin per se was administered.

61 Claims, No Drawings

PRO-DRUG FORMS OF DIGOXIN AND METHOD OF PREPARING AND USING SAME

BACKGROUND OF THE INVENTION

1. FIELD OF THE INVENTION

Th present invention is directed to novel pro-drug forms of digoxin and namely, the mono- through penta-ester derivatives thereof formed by the reaction of digoxin with a naturally occurring or synthetic amino acid.

As employed in this application, the term "pro-drug" denotes an art recognized expression, indicating that a derivative of a proven and known drug has been prepared, which after administration in suitable dosage form, will "cleave" in the body, thus releasing the basic drug. The higher solubility and/or better absorption characteristics of the pro-drug in conjuction with protecting, in the pro-drug, the active sites of the molecule against undesired metabolic pathways will permit such drug to obtain a higher and more reproducible bioavailability level than that which could be obtained if the basic drug per se were administered. Thus, in the instant application, the derivatives described above will permit digoxin to attain a superior bioavailability level in the bloodstream, than that which could be obtained if digoxin were administered per se.

2. DESCRIPTION OF THE PRIOR ART

Digoxin is a cardiotonic drug, used in the field of medicine to achieve an increase in the force of myocardial contraction. Basically, digoxin is a conduction system depressant which acts in such a manner as to decrease cardiac rate.

The structural formula for digoxin is set out below, and conventionally speaking, the dose administered to a patent (orally) to achieve digitialization is approximately 1.5 mg and thereafter, a maintenance dose of approximately 0.5 mg is required.

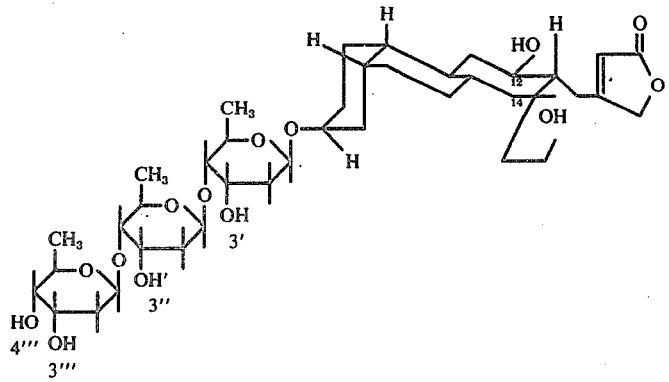

Digoxin is used in the treatment of cardiac failure, atrial fibrillation and flutter, paroxysinal tachycardia, cardiac insufficiency, etc. It has the advantage as compared to digitoxin, in that its onset of action is quite more rapid and further, its duration of action is shorter. It has an additional advantage in that in the event of an overdose, the symptoms associated therewith are more readily dissipated; however, digoxin is not as completely absorbed from the gastrointestinal tract as digitoxin. Essentially, digoxin is absorbed only to the extend of about 50% to 70%. Its solubility per ml of 0.1 N HCl is about 78 mcg. at 25° C.

The low solubility of digoxin in water and in other various media such as artificial gastric juice (e.g. 0.1 N HCl) has heretofore restricted its medicinal value. On the other hand, the therapeutic and toxic dose of digoxin are extremely close. Consequently, the difference in the absorption of digoxin observed (due to its low solubility) and its varying rate of absorption in different individuals, can cause toxic effects.

To date, numerous efforts have been directed to obtaining a derivative of digoxin exhibiting favorable physical properties, which would permit such derivatives to be administered for the purpose of enabling digoxin to be released in the bloodstream at a high bioavailable level, without exhibiting accompanying toxic side effects. A review of the literature respective of these derivatives follows:

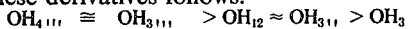

On the other hand, the digoxin molecule contains a base-sensitive lactone ring, which in basic solution or solutions, will undergo irreversible rearrangement. Strong acids, however, split off the digitoxose moieties.

Thus, the most reactive part of the molecule is the $3'''$ and $4'''$ hydroxy groups. A number of derivatives have been prepared by reacting the hydroxy groups in digoxin as outlined below.

U.S. Pat. No. 3,538,078, Belgian Pat. No. 752,284 and German Pat. No. 1,961,034 have disclosed digoxin ether derivatives of the $3'''$, $4'''$-mono-ether type, the di-ethers, and the mono-ethers-monoacylates. Specifically, the $3'''$-monethyl ether, the $3'''$k-monomethyl ether, the dimethyl ether, the monoacetyl-monoethyl ether, the monoformyl-monomethyl ether, the monoethoxyacetyl-monomethyl ether, the $4'''$-monomethyl ether, and the $4'''$-monoethyl ether have been disclosed.

Belgian Patent 672,307 discloses digoxin acylates, such as the tetraformate ($4'''$, $3'''$, $3'$ and $3''$).

Belgian Pat. No. 750,875 and German Pat. No. 2,019,967 disclose digoxin derivatives of the pentanitrate and mono-di and -tetranitrate type.

Belgian Patent 763,817 discloses digoxin derivatives of the $3'''$ and $4'''$-monoacylate type, employing an alkyl-ortho-acetate. The same compounds are disclosed as being derived from the separation of same out of a mixture of glucosides in French Pat. No. 1,568,075.

Other $3'''$-monoacylates of the formula:

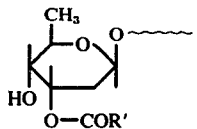

are known wherein R' represents a substituted alkyl group of from one to four carbon atoms, whose substituents are either a halogen atom, an aryl group (preferably a phenyl group) or a cycloalkyl group; a straight alkyl group of from 2 to 12 carbon atoms, or a cycloalkyl group of from three to eight carbon atoms. See, German Patent No. 2,101,595.

U.S. Pat. No. 3,514,441 discloses 12-monoacylates of digoxin obtained by protecting the 3''' and 4''' hydroxy groups by forming a 3''' or 4'''-carbonate or a 3''',4'''-cyclocarbonate. The aforementioned protecting groups can easily be removed, selectively, following acylation of the $C_{12}$ hydroxy group.

A number of digoxin derivatives have been prepared in the prior art by effecting structural changes of the steroid part, such as the digoxin 15',16'-diacetates. For instance, see Belgian Pat. No. 749,680.

Belgian Patent 751,768 discloses the 22-n-butoxy; the 22-fluoro; and the 22-methoxy forms of digoxin.

German Patent 2,052,634 discloses derivatives substituted on the lactone ring of digoxin by a group of the —HC=C($R_1,R_2$) type, wherein $R_1$ represents a CN group, a COOH group, and a carboalkoxy group, and wherein $R_2$ represents a hydrogen atom, a flourine atom, a chlorine atom, an alkyl group, an alkoxy group, or a CN group.

Dutch Pat. No. 66-01041 discloses 12-dehydro digitoxin and Swiss Pat. No. 413,812 discloses dihydrodigoxin.

Finally, United States Patent 3,696,091 discloses 22-substituted (F, Cl, alkoxy) digoxin ether and acylates.

Since the inventor's main objective concerned the development of transient digoxin derivatives having higher water solubility and absorption characteristics (higher bioavailability levels), he was extremely interested in only the activity and physical properties of the simple reported digoxin derivatives, i.e., the ethers and acylates.

While all reported derivatives thus prepared in the prior art are claimed to exhibit superior therapeutic and/or physicochemical properties than digoxin per se, this is not exactly true. For instance, it is still questionable whether digoxin ethers are hydrolyzed anzymatically. Recent reports seem to indicate that 4'''-methyl-digoxin is actually demethylated in man. In this regard, reference is made to the articles by H. Rennekamp, C. H. Rennekamp, U. Abshagen, K. V. Bergmann, and N. Rietbrock, *Arch. Pharmacol*, 273, 172 (1972) and N. Reitbrock, C. H. Rennekamp, H. Rennekamp, K. V. Bergmann and U. Abshagen ibid, 272, 450 (1972) respectively.

However, more recent studies conclude that "beta-methyldigoxin is very resistant to degradation by animal enzymes. Methyl digoxin is a new glycoside, but not a form of digoxin which exhibits improved absorption, i.e., bioavailability. The metabolism of digoxin appears to be inhibited by substituting the beta-hydroxy group of the third digitoxose molecule." On the other hand, it is generally accepted that acetyl digoxin is rapidly hydrolyzed giving rise to digoxin. See, G. Haberland, *Arzneimittel Forsch*, 15, 481 (1965); K. Buchtela, U. Drexler, H. Hackl, N. Konigstein, and O. Schlager, ibid, 18, 295 (1968); and W. Forster and S. Schulzeck, *Biochem. Pharmacol*., 17, 489 (1968).

United States Patent 3,884,905, in the name of the present inventor, discloses the mono- through penta-nocotinate, isonicotinate and picolinate derivatives of digoxin.

SUMMARY OF THE INVENTION

It is an object of the present invention to provide new derivatives of digoxin for administration to warm-blooded animals, e.g., humans, and more particularly, it is the primary object of the present invention to provide new "pro-drug" forms of digoxin which when introduced into the stomach of a warm-blooded animal will exhibit superior solubilization therein (as evidenced by the solubility of these forms in 0.1 N HCl) to the extent that superior bioavailability of digoxin, following "cleavage" of the derivative can be achieved. At this juncture, it should be emphasized that the solubility of the compounds of the present invention is independent of pH. That is, superior solubility is observed throughout the entire spectrum of the pH range.

Accordingly, this invention is concerned with the discovery of new digoxin derivatives and specifically, digoxin derivatives containing a naturally occurring amino acid residue or a

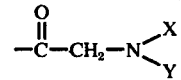

group (mono- through penta-) as set forth in the following formula wherein X and Y are defined infra:

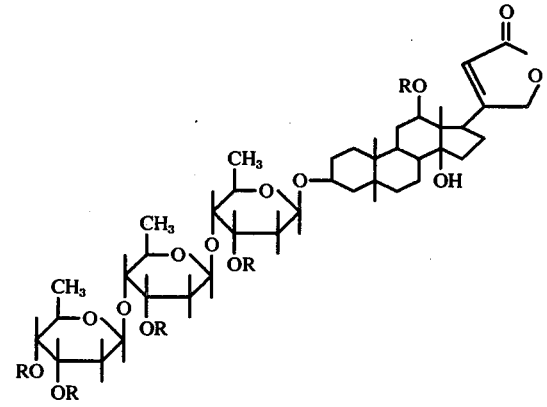

wherein R represents a member selected from the group consisting of a hydrogen atom, a residue of any naturally occurring amino acid, and a

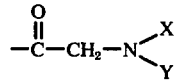

group, wherein X and Y, which may be the same or different, each represent a member selected from the group consisting of a methyl group and an ethyl group, or wherein X and Y may form a $(CH_2)_4$ or $(CH_2)_5$ heterocyclic ring with the N atom to which each set of X and Y are attached, and a non-toxic inorganic or organic pharmaceutically acceptable acid addition salt thereof, with the proviso that:

when R is a member other than a hydrogen atom, all of said R's must be the same member.

In the above formula, when R is any member other than a hydrogen atom, for example, an N,N-dimethylaminoglycyl group, all of said R's must be the same member, i.e., an N,N-dimethylaminoglycyl group.

As used herein, the phrase "non-toxic inorganic or organic pharmaceutically acceptable acid addition salt" generally includes the non-toxic acid addition salts of the compounds of the above formula, formed with non-toxic inorganic salts or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, toluene-sulfonic, and the like.

Similarly, the term "natural occurring amino acid" means any natural α-amino acid which occurs in proteins, including without limitation, glycine, alanine, valine, leucine, isoleucine, cysteine, cystine, methionine, serine, threonine, aspartic acid, glutamic acid, arginine, lysine, hydroxylsine, phenylalanine, tyrosine, asparagine, glutamine, proline, hydroxyproline, histidine, tryptophan, and pyroglutamic acid.

DETAILED DESCRIPTION OF THE INVENTION

Using stoichiometric amounts of each reactant, the digoxin derivatives of this invention can be prepared in accordance with the procedures outlined below.

NATURALLY OCCURRING AMINO ACID DERIVATIVES

Under the conditions of room temperature and standard pressure, digoxin is initially dissolved in a suitable solvent such as pyridine and subsequently, the corresponding N-protected naturally occuring amino acid anhydride is added thereto and the overall mixture is permitted to stand, following stirring, for several days. Subsequently, the reaction mixture is introduced into a suitable amount of water with stirring. A fine precipitate will be observed, and such precipitate is floated off, washed five times with water and then dried over calcium chloride. At this point in time, the crude digoxin derivative has been obtained and subsequently, if necessary, this crude material can be dissolved in a suitable amount of a chloroform/methanol mixture, chromatographed, after which, the solvent is evaporated off to dryness to thus yield the final pure digoxin derivative.

In an alternative method, the naturally occurring amino acid derivatives can be prepared by reacting digoxin with a suitable N-protected amino acid, wherein the protective group can be removed via hydrolysis or hydrogenolysis. Illustrative of such protective groups are carbobenzoxy, formyl, and the like. The reaction is carried out by employing a generally accepted coupling procedure such as the "mixed" anhydride method, acyl chloride method, or by employing selected coupling agents such as dicyclohexylcarbodiimide (DCCI) or N-ethoxy-carbonyl-2-ethoxy-1,3-dihydroquinoline (EEDQ). This reaction is carried out at standard pressure and at a temperature of from 0° C to room temperature in the presence of a suitable organic solvent such as tetrahydrofuran, dioxane, dichloromethane and the like, for a period of one to 24 hours. The protective groups of the amino acid esters are then cleaved conventionally via hydrolysis or hydrogenolysis, provided that the conditions do not effect the lactone ring in the digoxin molecule (for example, basic conditions which would open up the lactone ring, cannot be employed).

In still yet another alternative preparatory embodiment, the naturally occurring amino acid derivatives of the present invention can be prepared in accordance with the step-wise procedure first recited above, substituting the corresponding amino acid hydrochloride for the anhydride and employing as the reaction solvent, chloroform of any other suitable organic solvent (methylene chloride, carbon tetrachloride, tetrahydrofuran, etc.), the reaction mixture being refluxed at room temperature for a period of from one to two hours and said reaction being carried out at room temperature and standard pressure.

N,N-DIALKYLAMINO ACID DERIVATIVES

For the preparation of the N,N-dialkylamino acid derivatives, the acid anhydride or the acyl chloride methods described above can be employed.

One special and novel feature of the present invention is the realization that these N,N-dialkylamino acid esters can be prepared directly by using the N,N-dialkylamino acid or its HX salt (wherein HX represents a non-toxic inorganic or organic pharmaceutically acceptable acid addition salt as defined earlier) in the presence of a weak organic base-solvent, e.g., pyridine, quinoline, isoquinoline, N-methylpyrrole or any other equivalent organic base-solvent), and a suitable coupling agent such as DCCI or EEDQ. Preferably, however, a carbodiimide type coupling agent such as DCCI is introduced. The reaction is carried out at room temperature and at standard pressure for over a period of from 1 hour to 4 days.

One interesting additional feature observed was the extent to which acylation of the digoxin moiety could be controlled by altering the mole ratio of the N,N-dialkylamino acid and of the coupling agent employed. Thus, with a ratio of 1:1 and 1:2, the more desired mono- and/or di-acylated digoxin derivatives could be prepared. Increasing the ratio to 1:3, 1:4 and 1:5 will yield the corresponding tri-, tetra- and penta- acylated derivatives.

The final compounds can be isolated from the reaction mixture after removing the urea derivative formed (by filtration), by evaporation of the organic base-solvent employed or by precipitating the digoxin acylate in water.

The digoxin derivatives of the present invention are generally administered orally, for instance, in the form of a pharmaceutically acceptable tablet comprising the particular digoxin derivative and a pharmaceutically acceptable inert diluent. However, it is also apparent that other routes of administration are available as well.

The pharmaceutical dose required will naturally vary, depending upon the need, size and weight of the individual. However, as a basic guideline, dosage levels are comparable to the wellknown dosage levels for digoxin. See, *The Pharmacologic Basis of Therapeutics*, Goodman and Gillman, 1965, pg. 691 and *Physicians' Desk Reference*, 29th Edition, 1975, pg. 669, respectively. Accordingly, the compounds of the present invention could be administered, for example, as a tablet containing the equivalent of 250 or 500 micrograms of digoxin.

Without further elaboration, it is believed that one of ordinary skill in the art can, using the preceding description, utilize the present invention to its fullest extent. The following specific embodiments are, therefore, to be simply construed as merely illustrative, and not limitative of the remainder of the specification and claims in any way whatsoever.

EXAMPLE I

DIGOXIN MONO-N,N-DIMETHYL)-GYLCINATE 7.8 g of digoxin (0.01 mol) was dissolved in 175 ml of pyridine and 4.53 g (0.022 mol) of dicyclohexylcarbodiimide (DCCI), and 2.79 g (0.02 mol) of N,N-dimethylglycine hydrocholride added thereto. The resulting mixture was stirred at room temperature for 20 hours. During this period, all of the digoxin was reacted as indicated by Thin Layer Chromatograph analysis (acetone:hexane = 40:60 mobile phase). The Majority of the solvent was removed in vacuo and the residue was then extracted with dichloromethane. The dichloromethane was then filtered off, washed with water, and evaporated to dryness. There were obtained 5.80 g (67% yield) of digoxin mono- (N,N-dimethyl)-glycinate. Mp 107-109° C.

Anal. Calcd for $C_{45}H_{71}O_{15}N$: C, 62.40; H, 8.26; N, 1.62.

Found: C, 62.06; H, 8.37; N, 1.51.

Alternatively, the same compound can be obtained by precipitating the reaction mixture in water, washing the precipitate with tetrahydrofuran and isolating the title compound by evaporation of the tetrahydrofuran solution.

When obtained, the compound was dissolved in 0.01 N HCl and a solubility value of 12.6 mg/ml was obtained. Essentially, the same solubility (12.2 mg/ml) was obtained at a pH of 3 using a citrate buffer.

The solubility value for digoxin in the same medium is about 78 mcg/ml.

By following the same reaction procedure of Example I and substituting the generically or specifically described reactants and/or operating conditions of this invention for those used in the preceding example, the following additional compounds are obtained:
(1) Digoxin mono- (N,N-diethyl)-glycinate.
(2) Digoxin mono- (1-piperidly)-acetate.

By again following the reaction scheme of Example I, and substituting the generically or specifically described reactants and/or operating conditions of this invention for those used therein, and further increasing the reaction time to four (4) days, the corresponding di-derivatives of digoxin in accordance with the present invention can be obtained:
(1) Di-(N,N-dimethyl)glycinate.
(2) Di-(N,N-diethyl(glycinate.
(3) Di-(1-piperidyl)acetate.

EXAMPLE II

DIGOXIN MONO-N-FORMYLGLYCINATE

By reproducing Example I, but replacing N,N-dimethylglycine hydrochloride with N-formylglycine, the above-titled compound is obtained.

Similarly, by extending the reaction time, di-N-formylglycinate is obtained.

All the remaining mono- through penta- derivatives of the present application can be obtained by simply substituting the generically or specifically described reactants and/or operating conditions of this invention for those in the preceding examples. For instance, digoxin tetra-(N,N-dimethyl)-glycinate, digoxin penta-(N,N-dimethyl)-glycinate, digoxin tetra-(1-piperidyl)-acetate, digoxin penta-1-piperidyl)-acetate, digoxin tri-N-formylglycinate, digoxin tetra-N-formylglycinate and digoxin penta-N-formylglycinate are so prepared.

The remaining compounds of the present invention exhibit substantially the same solubility as that exhibited for the title compound of Example I, digoxin mono-(N,N-dimethyl-glycinate.

In summary then, specific novel digoxin derivatives have been prepared, which owing to their extreme solubility over a wide pH range, can be expected to provide enhance digoxin bioavailability when cleaved following absorption in comparison to digoxin per se.

As stated earlier, the pro-drug forms of this invention are suitably and generally administered in oral dosage form, such as by tablet or capsule, by combining the same in a cardiotonic effective amount with any oral pharmaceutically acceptable inert diluent, such as lactose, starch (pharmaceutical grade), dicalcium phosphate, calcium sulfate, kaolin, mannitol and powdered sugar. In addition, when required, suitable binders, lubricants, disintegrating agents, and coloring agents can also be added. Typical binders include starch, gelatin, sugars, such as sucrose, molasses, and lactose, natural and synthetic gums such as acacia, sodium alginate, extract of Irish moss, carboxymethylcellulose, methylcellulose, and polyvinylpyrrolidone, polyethylene glycol, ethylcellulose and waxes. Typical lubricants for use in these dosage forms can include, without limitation, boric acid, sodium benzoate, sodium acetate, sodium chloride, leucine, and polyethylene glycol. Suitable disintegrators can include, without limitation, starch, methylcellulose, agar, bentonite, cellulose and wood products, alginic acid, guar gum, citris pulp, carboxymethylcellulose, and sodium lauryl sulfate. If desired, a conventionally pharmaceutically acceptable dye can be incorporated into the dosage unit form, e.g., any of the standard FD&C dyes.

Any skilled artisan can prepare these oral dosage forms by simply referring to the oral dosage form preparatory procedure outlined in REMINGTON'S PHARMACEUTICAL SCIENCES, Fourteenth Edition (1970), pages 1659 through 1698 inclusive.

From the foregoing description, one skilled in the art can easily ascertain the essential characteristics of this invention, and without departing from the spirit and scope thereof, can make various changes and/or modifications to the invention for adapting it to various usages and conditions. As such, such changes and modifications are properly, equitably and intended to be, within the full range of equivalence of the following claims.

What I claim is:
1. A pro-drug of digoxin having the formula:

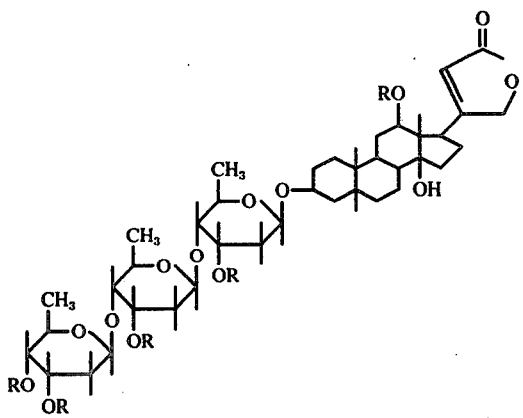

wherein R represents a member selected from the group consisting of a hydrogen atom, a residue of any naturally occurring protein amino acid, and a

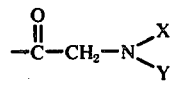

group, wherein X and Y, which may be the same or different, each represent a member selected from the group consisting of a methyl group and an ethyl group, or wherein X and Y may form a (CH$_2$)$_4$ or (CH$_2$)$_5$ heterocyclic ring with the N atom to which each of X and Y are attached, and a non-toxic inorganic or organic pharmaceutically acceptable acid addition salt thereof, with the proviso that:

when R is a member other than a hydrogen atom, all of said R's must be the same member.

2. The compound of claim 1, wherein R represents a

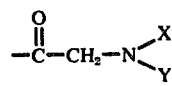

group and X and Y represent a methyl group.

3. The compound of claim 1, wherein R represents a

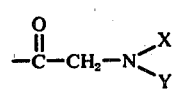

group and X and Y represents an ethyl group.

4. The compound of claim 1: Digoxin mono-(N,N-dimethyl)-glycinate.

5. The compound of claim 1: Digoxin mono-(N,N-diethyl)-glycinate.

6. The compound of claim 1: Digoxin mono-(1-piperidyl)-acetate.

7. The compound of claim 1: Digoxin-di-(N,N-dimethyl)-glycinate.

8. The compound of claim 1: Digoxin-di-(N,N-diethyl)-glycinate.

9. The compound of claim 1: Digoxin-di-(1-piperidyl)-acetate.

10. The compound of claim 1: Digoxin mono-N-formylglycinate.

11. The compound of claim 1: Digoxin di-N-formlglycinate.

12. The compound of claim 1: Digoxin tetra-(N,N-dimethyl)-glycinate.

13. The compound of claim 1: Digoxin penta-(N,N-dimethyl)-glycinate.

14. The compound of claim 1: Digoxin tetra-(1-piperidyl)-acetate.

15. The compound of claim 1: Digoxin penta-(1-piperidyl)-acetate.

16. The compound of claim 1: Digoxin tri-N-formyl-glycinate.

17. The compound of claim 1: Digoxin tetra-N-formylglycinate.

18. The compound of claim 1: Digoxin penta-N-formylglycinate.

19. A pharmaceutcial composition consisting essentially of a pharmaceutically acceptable oral inert diluent and a cardiotonic effective amount of a pro-drug of digoxin having the formula:

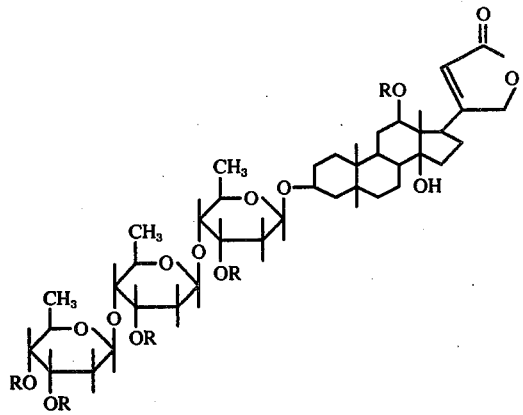

wherein R represents a member selected from the group consisting of a hydrogen atom, a residue of any naturally occurring protein amino acid, and a

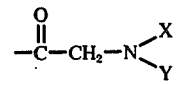

group, wherein X and Y, which may be the same or different, each represent a member selected from the group consisting of a methyl group and an ethyl group, or wherein X and Y may form a (CH$_2$)$_4$ or (CH$_2$)$_5$ heterocyclic ring with the N atom to which they are attached, and a non-toxic inorganic or organic pharmaceutically acceptable acid addition salt thereof, with the proviso that:

when R is a member other than a hydrogen atom, all of said R's must be the same member.

20. The composition of claim 19, wherein said compound is: Digoxin mono-(N,N-dimethyl)-glycinate.

21. Th composition of claim 19, wherein said compound is: Digoxin mono(N,N-diethyl)-glycinate.

22. The composition of claim 19, wherein said compound is: Digoxin mono-(1-piperidyl)-acetate.

23. Th composition of claim 19, wherein said compound is: Digoxin-di-(N,N-dimethyl)-glycinate.

24. The composition of claim 19, wherein said compound is: Digoxin-di-(N,N-diethyl)-glycinate.

25. The composition of claim 19, wherein said compound is: Digoxin-di-(1-piperidyl)-acetate.

26. The composition of claim 19, wherein said compound is: Digoxin mono-N-formylglycinate.

27. The composition of claim 19, wherein said compound is: Digoxin tetra-(N,N-dimethyl)-glycinate.

28. The composition of claim 19, wherein said compound is: Digoxin penta-(N,N-dimethyl)-glycinate.

29. The composition of claim 19, wherein said compound is: Digoxin tetra-(1-piperidly)-acetate.

30. The composition of claim 19, wherein said compound is: Digoxin penta-(1-piperidyl)-acetate.

31. The composition of claim 19, wherein said compound is: Digoxin tri-N-formylglycinate.

32. The composition of claim 19, wherein said compound is: Digoxin tetra-N-formylglycinate.

33. The composition of claim 19, wherein said compound is: Digoxin penta-N-formylglycinate.

34. A method for treating cardiac insufficiency in a warm-blooded animal which comprises orally administering thereto, an effective cardiontonic amount of a pro-drug of digoxin having the following formula:

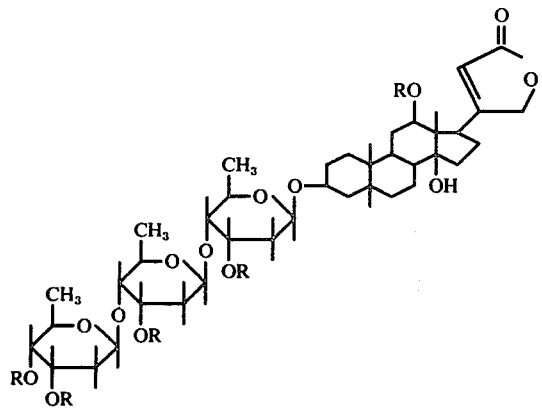

wherein R represents a member selected from the group consisting of a hydrogen atom, a residue of any naturally occurring protein amino acid, and a

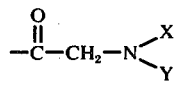

group, wherein X and Y, which may be the same or different, each represent a member selected from the group consisting of a methyl group and an ethyl group, or wherein X and Y may form a $(CH_2)_4$ or $(CH_2)_5$ heterocyclic ring with the N atom to which they are attached, and a non-toxic inorganic or organic pharmaceutically acceptable acid addition salt thereof, with the proviso that:

when R is a member other than a hydrogen atom, all of said R's must be the same member.

35. Th method of claim 34, wherein said compound is: Digoxin mono-(N,N-dimethyl)-glycinate.

36. The method of claim 34, wherein said compound is: Digoxin mono-(N,N-diethyl)-glycinate.

37. The method of claim 34, wherein said compound is: Digoxin mono-(1-piperidyl)-acetate.

38. The method of claim 34, wherein said compound is: Digoxin-di-(N,N-dimethyl)-glycinate.

39. The method of claim 34, wherein said compound is: Digoxin-di-(N,N-dithyl)-glycinate.

40. The method of claim 34, wherein said compound is: Digoxin-di-(1-piperidyl)-acetate.

41. The method of claim 34, wherein said compound is: Digoxin mono-N-formylglycinate.

42. The method of claim 34, wherein said compound is: Digoxin di-N-formylglycinate.

43. The method of claim 34, wherein said compound is: Digoxin tetra-(N,N-dimethyl)-glycinate.

44. The method of claim 34, wherein said compound is: Digoxin penta-(N,N-dimethyl)-glycinate.

45. The method of claim 34, wherein said compound is: Digoxin tetra-(1-piperidyl)-acetate.

46. The method of claim 34, wherein said compound is: Digoxin penta-(1-piperidyl)-acetate.

47. The method of claim 34, wherein said compound is: Digoxin tri-N-formylglycinate.

48. The method of claim 34, wherein said compound is: Digoxin tetra-N-formylglycinate.

49. The method of claim 34, wherein said compound is: Digoxin penta-N-formylglycinate.

50. The method of claim 34, wherein said compound is maintained in combination with a pharmaceutically acceptable oral inert diluent.

51. The method of claim 34, wherein said compound is present in an amount of from 250 to 500 micrograms.

52. The method of claim 50, wherein said compound is present in an amount of from 250 to 500 micrograms.

53. A method for preparing a pro-drug compound of digoxin having the formula:

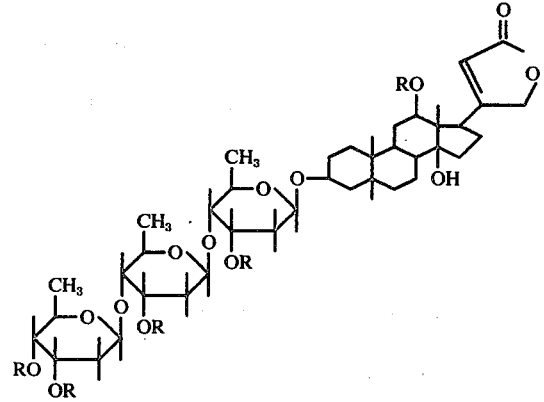

where R represents a

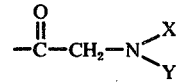

group, wherein X and Y, which may be the same or different, each represent a member selected from the group consisting of a methyl group and an ethyl group, or wherein X and Y may form a $(CH_2)_4$ or $(CH_2)_5$ heterocyclic ring with the N atom to which each of X and Y are attached, with the proviso that when R is a member other than a hydrogen atom, all of said R's must be the same member which comprises the steps of 1. reacting, in the presence of a suitable organic coupling agent and a weak organic base-solvent, a stoichiometric amount of digoxin with a stoichiometric amount of an N,N-dialkylamino acid having the formula

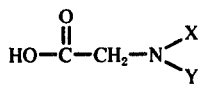

or its pharmaceutically acceptable acid addition salt, wherein X and Y, which may be the same or different, each represent a member selected from the group consisting of a methyl group and an ethyl group, or wherein X and Y may form a $(CH_2)_4$ or $(CH_2)_5$ heterocyclic ring with the N atom to which they are attached, said reaction being carried out at room temperature, standard pressure and over a period of time of from one hour to four days, and wherein the mole ratio of said N,N-dialkylamino acid to said coupling agent ranges from 1:1 to 1:5, and 2. removing the final product thus formed during the reaction step (1) above from the reaction mixture.

54. The method of claim 53, wherein said weak organic base-solvent is a member selected from the group consisting of pyridine, quinoline, isoquinoline, and N-methylpyrrole.

55. The method of claim 53, wherein said coupling agent is a member selected from the group consisting of dicyclohexylcarbodiimide and N-ethoxy-carbonyl-2-ethoxy-1,3-dihydroquinoline.

56. The method of claim 53, wherein the mole ratio of said N,Nj-dialkylamino acid to said coupling agent is 1:1.

57. The method of claim 53, wherein the mole ratio of said N,N-dialkylamino acid to said coupling agent is 1:2.

58. The method of claim 53, wherein the mole ratio of said N,N-dialkylamino acid to said coupling agent is 1:3.

59. The method of claim 53, wherein the mole ratio of said N,N-dialkylamino acid to said coupling agent is 1:4.

60. The method of claim 53, wherein the mole ratio of said N,N-dialkylamino acid to said coupling agent is 1:5.

61. The method of claim 53, wherein said pro-drug compound is further reacted with a non-toxic pharmaceutically acceptable acid, thus forming the corresponding non-toxic pharmaceutically acceptable acid addition salt.

* * * * *